(12) United States Patent
Hood et al.

(10) Patent No.: US 10,607,471 B2
(45) Date of Patent: **\*Mar. 31, 2020**

(54) HAND HYGIENE MONITORING SYSTEM WITH CUSTOMIZABLE THRESHOLDS

(71) Applicant: Hill-Rom Services, Inc., Batesville, IN (US)

(72) Inventors: Michael S. Hood, Batesville, IN (US); Ryan M. Madigan, Raleigh, NC (US); Joshua P. Lingenfelser, Fuquay Varina, NC (US); Kirsten M. Emmons, Batesville, IN (US); Kelly F. Walton, Cary, NC (US); Christopher J. Skotnicki, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 112 days.

This patent is subject to a terminal disclaimer.

(21) Appl. No.: 15/270,330

(22) Filed: Sep. 20, 2016

(65) Prior Publication Data

US 2017/0098366 A1 Apr. 6, 2017

Related U.S. Application Data

(60) Provisional application No. 62/297,366, filed on Feb. 19, 2016, provisional application No. 62/237,647, filed on Oct. 6, 2015.

(51) Int. Cl.
*G08B 21/24* (2006.01)
*G16H 40/20* (2018.01)

(52) U.S. Cl.
CPC .......... *G08B 21/245* (2013.01); *G16H 40/20* (2018.01)

(58) Field of Classification Search
CPC .......................... G08B 21/245; G06F 19/327
See application file for complete search history.

(56) References Cited

U.S. PATENT DOCUMENTS

| 4,275,385 A | 6/1981 | White |
| 4,601,064 A | 7/1986 | Shipley |

(Continued)

FOREIGN PATENT DOCUMENTS

| DE | 19903079 | 8/2000 |
| GB | 2324397 | 10/1998 |

(Continued)

OTHER PUBLICATIONS

European Search Report from EP 16 19 2282 dated Dec. 21, 2016, 10 pages.

(Continued)

*Primary Examiner* — James J Yang
(74) *Attorney, Agent, or Firm* — Barnes & Thornburg LLP

(57) ABSTRACT

Technologies for monitoring hand hygiene compliance of a user include a remote analysis server configured to receive an indication from a plurality of hand hygiene devices. The hand hygiene devices include one or more disinfectant hand rub dispensing devices and one or more soap dispensing devices. The remote analysis server is further configured to manage a compliance counter for the user based a number of times disinfectant hand rub dispensing device and compare the compliance counter to a non-compliance threshold of the hand hygiene policy. The remote analysis server is configured to transmit a notification of compliance or non-compliance based on whether the compliance counter is greater than or equal to the non-compliance threshold. A threshold of compliance is customizable based on a room type designation.

22 Claims, 7 Drawing Sheets

(56) References Cited

U.S. PATENT DOCUMENTS

| | | |
|---|---|---|
| 4,896,144 A | 1/1990 | Bogstad |
| 5,016,172 A | 5/1991 | Dessertine |
| 5,095,925 A | 3/1992 | Elledge et al. |
| 5,119,104 A | 6/1992 | Heller |
| 5,199,118 A | 4/1993 | Cole et al. |
| 5,202,666 A | 4/1993 | Knippscheer |
| 5,265,628 A | 11/1993 | Sage et al. |
| 5,276,496 A | 1/1994 | Heller et al. |
| 5,291,399 A | 3/1994 | Chaco |
| 5,355,222 A | 10/1994 | Heller et al. |
| 5,387,993 A | 2/1995 | Heller et al. |
| 5,426,425 A | 6/1995 | Conrad et al. |
| RE35,035 E | 9/1995 | Shipley |
| 5,455,851 A | 10/1995 | Chao et al. |
| 5,465,082 A | 11/1995 | Chao |
| 5,515,426 A | 5/1996 | Yacenda et al. |
| 5,548,637 A | 8/1996 | Heller et al. |
| 5,561,412 A | 10/1996 | Novak et al. |
| 5,572,195 A | 11/1996 | Heller et al. |
| 5,573,041 A | 11/1996 | Skell et al. |
| 5,594,786 A | 1/1997 | Chao et al. |
| 5,610,589 A | 3/1997 | Evans et al. |
| 5,633,742 A | 5/1997 | Shipley |
| 5,670,945 A | 9/1997 | Applonie |
| 5,689,229 A | 11/1997 | Chaco et al. |
| 5,694,323 A | 12/1997 | Koropitzer et al. |
| 5,695,091 A | 12/1997 | Winings et al. |
| 5,699,038 A | 12/1997 | Ulrich et al. |
| 5,702,115 A | 12/1997 | Pool |
| 5,745,272 A | 4/1998 | Shipley |
| 5,771,925 A | 6/1998 | Lewandowski |
| 5,774,865 A | 6/1998 | Glynn |
| 5,781,942 A | 7/1998 | Allen et al. |
| 5,785,181 A | 7/1998 | Quartararo, Jr. |
| 5,793,653 A | 8/1998 | Segal |
| 5,808,553 A | 9/1998 | Cunningham |
| 5,812,059 A | 9/1998 | Shaw et al. |
| 5,818,617 A | 10/1998 | Shipley |
| 5,822,418 A | 10/1998 | Yacenda et al. |
| 5,822,544 A | 10/1998 | Chao et al. |
| 5,823,447 A | 10/1998 | Maybach |
| 5,838,223 A | 11/1998 | Gallant et al. |
| 5,862,546 A | 1/1999 | Kim |
| 5,900,067 A | 5/1999 | Jones |
| 5,900,801 A | 5/1999 | Heagle et al. |
| 5,939,974 A | 8/1999 | Heagle et al. |
| 5,945,910 A | 8/1999 | Gorra |
| 5,952,924 A | 9/1999 | Evans et al. |
| 5,954,069 A | 9/1999 | Foster |
| 5,960,991 A | 10/1999 | Ophardt |
| 5,966,753 A | 10/1999 | Gauthier et al. |
| 6,000,429 A | 12/1999 | Van Marcke |
| RE36,530 E | 1/2000 | Heller et al. |
| 6,031,461 A | 2/2000 | Lynn |
| 6,038,331 A | 3/2000 | Johnson |
| 6,104,295 A | 8/2000 | Gaisser et al. |
| 6,125,482 A | 10/2000 | Foster |
| 6,147,607 A | 11/2000 | Lynn |
| 6,154,139 A | 11/2000 | Heller |
| 6,195,588 B1 | 2/2001 | Gauthier et al. |
| 6,211,788 B1 | 4/2001 | Lynn et al. |
| 6,219,164 B1 | 4/2001 | Morgaine |
| 6,236,317 B1 | 5/2001 | Cohen et al. |
| 6,236,953 B1 | 5/2001 | Segal |
| 6,278,372 B1 | 8/2001 | Velasco, Jr. et al. |
| 6,283,759 B1 | 9/2001 | Price et al. |
| 6,377,868 B1 | 4/2002 | Gardner, Jr. |
| 6,392,546 B1 | 5/2002 | Smith |
| 6,399,853 B1 | 6/2002 | Roe et al. |
| 6,404,837 B1 | 6/2002 | Thompson et al. |
| 6,426,701 B1 | 7/2002 | Levy et al. |
| 6,485,979 B1 | 11/2002 | Kippenhan et al. |
| 6,519,505 B2 | 2/2003 | Formon |
| 6,524,390 B1 | 2/2003 | Jones |
| 6,718,341 B1 | 4/2004 | Berstis et al. |
| 6,727,818 B1 | 4/2004 | Wildman et al. |
| 7,015,816 B2 | 3/2006 | Wildman et al. |
| 7,248,933 B2 | 7/2007 | Wildman |
| 7,408,470 B2 | 8/2008 | Wildman et al. |
| 7,450,024 B2 | 11/2008 | Wildman et al. |
| 7,812,730 B2 | 10/2010 | Wildman et al. |
| 8,368,544 B2 | 2/2013 | Wildman et al. |
| 8,598,996 B2 | 12/2013 | Wildman et al. |
| 2006/0132316 A1 | 6/2006 | Wildman et al. |
| 2008/0001763 A1 | 1/2008 | Raja et al. |
| 2009/0195385 A1 | 8/2009 | Huang et al. |
| 2010/0188228 A1* | 7/2010 | Hyland ............... G08B 21/245 340/573.1 |
| 2010/0315243 A1 | 12/2010 | Tokhtuev et al. |
| 2013/0027199 A1* | 1/2013 | Bonner ................ G08B 21/24 340/539.11 |
| 2013/0120142 A1 | 12/2013 | Wildman et al. |
| 2014/0081653 A1 | 3/2014 | Davis et al. |
| 2017/0076042 A1* | 3/2017 | Katz .................... G08B 21/245 |

FOREIGN PATENT DOCUMENTS

| | | |
|---|---|---|
| GB | 2328867 A | 3/1999 |
| WO | WO 93/10311 | 5/1993 |
| WO | WO 97/31350 | 8/1997 |

OTHER PUBLICATIONS

Carol Hildenbrand, *One Hand Better Wash the Other*, CIO Enterprise, Oct. 15, 1997 (1 page).

Kathleen G. Tatterson, *Employees Can't Wash Away Restroom Sensor*, Photonics Spectra, Jul. 1997 (1 page).

Marian Burros, *Wash Up: Big Brother Is Now in the Bathroom*, New York Times, Nov. 19, 1997 (1 page).

John Hendren, *Hand-washing detection system to get dirt on employees*, Business @marillo Globe-News, May 20, 1997 (3 pages).

Robert O'Harrow Jr., *Big Brother in the Bathroom?*, Washingtonpost.com, Aug. 30, 1997; p. A01 (3 pages).

Joni A. Mayer et al., *Increasing Handwashing in an Intensive Care Unit*, Infection Control 1986NoI. 7, No. 5 (4 pages).

Elaine Larson et al., *Effect of an Automated Sink on Handwashing Practices and Attitudes in High-Risk Units*, Infection Control and Hospital Epidemiology, Jul. 1991 (7 pages).

Elaine Larson, *Hand Washing—It's Essential—Even When You Use Gloves*, American Journal of Nursing, Jul. 1989 (8 pages).

Marian K. Fox et al., *How Good Are Hand Washing Practices?*, American Journal of Nursing, Sep. 1974 (3 pages).

William M. Marcil, *Handwashing Practices Among Occupational Therapy Personnel*, The American Journal of Occupational Therapy, vol. 47, No. 6, Jun. 1993 (6 pages).

*High-tech Hygiene: Monitoring System to Badger Employees Who Don't Wash Hands*, The Spokesman—Review, Sep. 1, 1997 (2 pages).

Business Wire, *Net/Tech to unveil patented Hygiene Guard Hand-Washing Monitoring System at the National Restaurant Show*, Apr. 3, 1997 (2 pages).

Hygiene Guard description from the Captology website, Stanford University, http://www-pcd.standford.edu/captology/resources/cep/catalog/hg.html, Oct. 9, 1999 ("Captology"), available at https://web.archive.org/web/19991009104253/http0://www-pcd.stanford.edu/captology/resources/cep/catalog/hg.html (1 page).

Broughall, et al., "An automatic monitoring system for measuring handwashing frequency in hospital wards," Journal of Hospital Infection (1984) 5, 447-453, 7 pages.

Pittet, "Improving Adherence to Hand Hygiene Practice: A Multi-disciplinary Approach," Emerging Infectious Diseases, vol. 7, No. 2, Mar.-Apr. 2001, 7 pages.

"Gyro-Cell affiliate announces successful testing of world's first infrared hand washing monitoring system," memo, Business Wire, Inc., May 13, 1997, 1 page.

"Complaint," *Hill-Rom Company, Inc., Hill-Rom Services, Inc. and Hill-Rom Manufacturing, Inc.* Plaintiffs, v. *General Electric Company*, Defendant, filed May 2, 104—Case No. 2:14CV187.

(56) References Cited

OTHER PUBLICATIONS

"Plaintiffs Hill-Rom Company, Inc., Hill-Rom Services, Inc., and Hill-Rom Manufacturing, Inc.'s Motion for Preliminary Injunction," filed May 8, 2014, 8 pages.
"Memorandum of Law in Support of Plaintiff's Motion for Preliminary Injunction," filed May 8, 2014, 32 pages.
"Declaration of Timothy Wildman," filed May 8, 2014, 23 pages.
"Declaration of Robin A. Felder, Ph.D.," filed May 8, 2014, 100 pages.
"Defendant General Electric Company's Opposition to Hill-Ram's Motion for Preliminary Amendment," filed Jun. 23, 2014, 32 pages.
"Declaration of Gill R. Tsouri, PH.D.," filed Jun. 23, 2014, 91 pages.
"Reply in Support of Plaintiffs' Motion for Preliminary Injunction," filed Jul. 3, 2014, 31 pages.
"Reply Declaration of Bradley N. Reiff," filed Jul. 3, 2014, 25 pages.
"Reply Declaration of Adam McMullin," filed Jul. 3, 2014, 12 pages.
"Supplemental Declaration of Robin A. Felder, PHD," filed Jul. 3, 2014, 74 pages.
"Transcript of Proceedings," in in *Hill-Rom Company, Inc., et al. v. General Electric Company*, dated Jul. 7, 2014, 103 pages.
"Plaintiffs' Opening Brief on Claim Construction," *Hill-Rom Company, Inc., Hill-Rom Services, Inc., and Hill-Rom Manufacturing, Inc. v. General Electric Company*, Filed Jul. 24, 2014, 29 Pages.
"Defendant General Electric Company's Opening Claim Construction Brief," *Hill-Rom Company, Inc., Hill-Rom Services, Inc. and Hill-Rom Manufacturing, Inc. v. General Electric Company*, Filed Jul. 24, 2014, 33 pages.
"Plaintiff's Reply Brief on Claim Construction," in *Hill-Rom Company, Inc., et al. v. General Electric Company*, filed on Jul. 31, 2014, 20 pages.
"Defendant General Electric Company's Responsive Claim Construction Brief," in *Hill-Rom Company, Inc., et al. v. General Electric Company*, filed on Jul. 31, 2014, 18 pages.
"Transcript of Proceedings," in *Hill-Rom Company, Inc., et al. v. General Electric Company*, dated Aug. 6, 2014, 66 pages.
"Defendant General Electric Company's First Supplemental Objections and Responses to Plaintiffs' Interrogatories," in *Hill-Rom Company, Inc., et al. v. General Electric Company*, dated Aug. 8, 2014, 13 pages.
"Appendices C through C-11 to Defendant General Electric Company's First Supplemental Objections and Responses to Plaintiffs' Interrogatories," in *Hill-Rom Company, Inc., et al. v. General Electric Company*, dated Aug. 8, 2014, 180 pages.
"Appendices D through D-11 to Defendant General Electric Company's First Supplemental Objections and Responses to Plaintiffs' Interrogatories," in *Hill-Rom Company, Inc., et al. v. General Electric Company*, dated Aug. 8, 2014, 69 pages.
"General Electric Company's Answer, Defenses, and Counterclaims to Plaintiff's Complaint for Patent Infringement," in *Hill-Rom Company, Inc., et al. v. General Electric Company*, filed Aug. 15, 2014, 12 pages.
"Joint Stipulation and Agreed Order of Dismissal," in *Hill-Rom Services, Inc. v. General Electric Company*, dated Aug. 19, 2014 (2 pages).

* cited by examiner

FIG. 6

HAND HYGIENE MONITORING SYSTEM WITH CUSTOMIZABLE THRESHOLDS

CROSS REFERENCE TO RELATED APPLICATIONS

This application claims the benefit, under 35 U.S.C. § 119(e), of U.S. Provisional Application Nos. 62/297,366, filed Feb. 19, 2016 and 62/237,647, filed Oct. 6, 2015, each of which is hereby incorporated by reference herein in its entirety.

BACKGROUND

The present disclosure relates generally to hygiene monitoring systems, and more particularly to hand hygiene monitoring systems usable in healthcare facilities.

Hygiene monitoring systems are typically used in facilities (e.g., food handling/processing facilities, healthcare facilities, etc.) where proper hygiene is required, such as by state or federal regulations and/or company policies, for example (i.e., wherein more control is required than just self-monitoring). Accordingly, to adhere to the required hygiene regulations and/or policies, the hygiene monitoring systems generally monitor for compliance based on the required hygiene regulations or policies. To do so, the hygiene monitoring systems typically include a multitude of sensors that can be placed throughout the facility (e.g., in particular identified areas, on pertinent hygiene-related components, etc.) and communicate with a central processing facility, which can aggregate the sensor data and analyze the data for compliance. Further, staff members whose compliance is to be monitored can wear or otherwise carry identifying technologies, such as a radio-frequency identification (RFID) smartcard, a tag, or a badge that interfaces with the various sensors such that the data can be attributed to a particular member of the staff. As a result, each staff member can be provided with a notification (e.g., a visual and/or audible alert) that is indicative of that staff member's level of compliance or non-compliance.

SUMMARY

The present application discloses one or more of the features recited in the appended claims and/or the following features which, alone or in any combination, may comprise patentable subject matter.

According to a first aspect of the present disclosure, a method for monitoring hand hygiene compliance with a hand hygiene policy may include receiving, at a remote analysis server, an indication from a first hand hygiene device that a hand hygiene activity was performed by a user of the first hand hygiene device, wherein the indication includes an identifier of the first hand hygiene device and an identifier of the user. The method may further include determining, by a hand hygiene monitoring engine of the remote analysis server, whether the identifier of the first hand hygiene device corresponds to one of a disinfectant hand rub dispensing device or a soap dispensing device.

The method may additionally include incrementing, by the hand hygiene monitoring engine, a compliance counter based on the identifier of the user in response to a determination that the identifier of the first hand hygiene device corresponds to the disinfectant hand rub dispensing device. The method may further still include comparing, by the hand hygiene monitoring engine, the compliance counter to a non-compliance threshold of the hand hygiene policy. The method may yet further include transmitting, by the hand hygiene monitoring engine, a notification of non-compliance in response to a determination that the compliance counter is greater than or equal to the non-compliance threshold.

In some embodiments, the method may further include resetting, by the hand hygiene monitoring engine, the compliance counter associated with the user in response to a determination that the identifier of the first hand hygiene device corresponds to the disinfectant hand rub dispensing device.

In some embodiments, the method may further include transmitting, by the hand hygiene monitoring engine and in response to the compliance counter being reset, a notification of compliance to one or more visual indicators proximate to the user.

In some embodiments, transmitting the notification of non-compliance may include transmitting the notification of non-compliance to one or more visual indicators proximate to the user.

In some embodiments, the one or more visual indicators includes a visual indicator of at least one of a badge worn by the user, a wrist-worn device worn by the user, a mobile computing device carried by the user, the first hand hygiene device, another first hand hygiene device, and equipment in viewing proximity of the user.

In some embodiments, transmitting the notification of non-compliance may include transmitting the notification of non-compliance to one or more audible indicators proximately located near the user.

In some embodiments, the one or more audible indicators includes an audible indicator of at least one of a badge worn by the user, a wrist-worn device worn by the user, a mobile computing device carried by the user, the first hand hygiene device, another first hand hygiene device, and equipment in hearing proximity of the user.

In some embodiments, the method may further include, by the hand hygiene monitoring engine, the compliance counter to a warning threshold of the hand hygiene policy, wherein the warning threshold is less than the non-compliance threshold. The method may additionally include transmitting, by the hand hygiene monitoring engine, a warning notification of non-compliance in response to a determination that the compliance counter is greater than or equal to the warning threshold.

In some embodiments, transmitting the warning notification of non-compliance comprises transmitting the warning notification of non-compliance to one or more visual indicators proximate to the user.

According to another aspect of the present disclosure, a system may include a plurality of hand hygiene devices, wherein each of the plurality of hand hygiene devices includes a sensor capable of detecting a user at one of the plurality of hand hygiene devices during a usage of the one of the plurality of hand hygiene devices. Additionally, the system may include a remote analysis server communicatively coupled to each of the plurality of hand hygiene devices. The remote analysis server may include a hand hygiene monitoring engine that is configured to monitor hand hygiene compliance of each user based on a hygiene compliance policy and a compliance counter associated with each user. Each of the plurality of hand hygiene devices may be further configured to transmit to the remote analysis server an indication that a hand hygiene activity was performed by a user. The indication may include an identifier of the hand hygiene device and an identifier of the user.

The hand hygiene monitoring engine, in response to having received the indication, may determine whether the identifier of the hand hygiene device corresponds to a soap dispensing device or a disinfectant hand rub dispensing device. The hand hygiene monitoring engine may further increment a compliance counter based on the identifier of the user in response to a determination that the hand hygiene device corresponds to the disinfectant hand rub dispensing device. Additionally, the hand hygiene monitoring engine may compare a value of the compliance counter to a non-compliance threshold to determine whether the user is in compliance with the hygiene compliance policy. Further, the hand hygiene monitoring engine may transmit a notification of non-compliance in response to a determination that the value of the compliance counter is greater than or equal to the non-compliance threshold. The notification is usable by a receiving device to provide an indication to the user that the user is not in compliance with the hygiene compliance policy.

In some embodiments, the hand hygiene monitoring engine is further to reset the compliance counter associated with the user in response to a determination that the identifier of the first hand hygiene device corresponds to the disinfectant hand rub dispensing device.

In some embodiments, the hand hygiene monitoring engine is further to transmit, in response to the compliance counter being reset, a notification of compliance to one or more visual indicators proximate to the user.

In some embodiments, to transmit the notification of non-compliance comprises transmitting the notification of non-compliance to one or more visual indicators proximate to the user.

In some embodiments, the one or more visual indicators includes a visual indicator of at least one of a badge worn by the user, a wrist-worn device worn by the user, a mobile computing device carried by the user, the first hand hygiene device, another first hand hygiene device, and equipment in viewing proximity of the user.

In some embodiments, to transmit the notification of non-compliance comprises to transmit the notification of non-compliance to one or more audible indicators proximate to the user.

In some embodiments, the one or more audible indicators includes an audible indicator of at least one of a badge worn by the user, a wrist-worn device worn by the user, a mobile computing device carried by the user, the first hand hygiene device, another first hand hygiene device, and equipment in hearing proximity of the user.

In some embodiments, the hand hygiene monitoring engine is further to compare the compliance counter to a warning threshold of the hand hygiene policy, wherein the warning threshold is less than the non-compliance threshold and transmit a warning notification of non-compliance in response to a determination that the compliance counter is greater than or equal to the warning threshold.

In some embodiments, to transmit the warning notification of non-compliance comprises to transmit the warning notification of non-compliance to one or more visual indicators proximate to the user.

In some embodiments, the non-compliance threshold is determined based on a room type designation corresponding to the identifier of the hand hygiene device. In some embodiments, the non-compliance threshold is determined based on a room type designation corresponding to the identifier of the hand hygiene device.

In some embodiments, the room type designation is one of enteric and standard. In some embodiments, room type designation is enteric and the non-compliance threshold is determined to be one.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description refers to the following figures in which:

FIG. 6 is a pictorial view of a graphical display of the hand hygiene monitoring system of FIGS. 1 and 2 showing that information regarding hygiene events is accessible for evaluation and use, and showing that hygiene compliance thresholds are customizable according to a room type designation of each patient room;

DETAILED DESCRIPTION

Aspects of the present invention are described with reference to certain illustrative embodiments shown in the accompanying drawings and described herein.

In general, certain facilities employ various hygiene policies based on the type of product or service provided at or by the facility. For example, an employee in a consumable goods handling/processing facility, may be required to wash their hands after a trip to the restroom, or may be required to wear gloves, masks, hairnets, etc. to avoid contamination of the consumable goods being processed. In another example, in a hospital facility, the hospital staff may be required to adhere to a hygiene compliance policy, as members of the hospital staff are typically in contact with sick patients with a high level of frequency. In furtherance of the example, the hygiene compliance policy may be a hand hygiene policy that can consist of using gel-based, waterless, disinfectant hand rubs until the a staff member's hands are "visibly soiled," upon which the staff member may be required to wash their hands with a non-antibacterial soap and water. However, the antibacterial effectiveness of such gel-based, waterless, disinfectant hand rubs can be reduced in just a few applications (i.e., well before the staff member's hands can become "visibly soiled").

Figure 1:
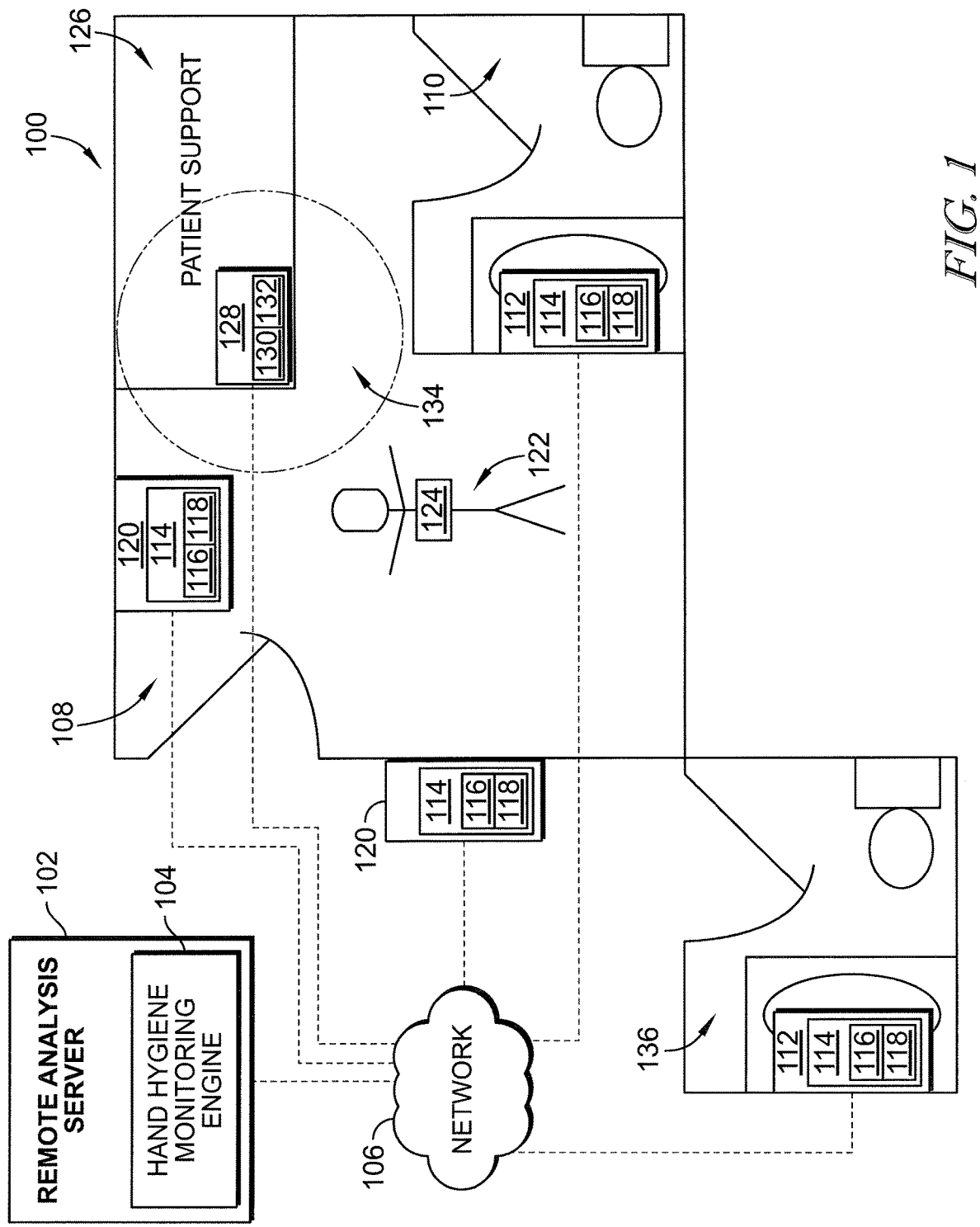
FIG. 1 is a block diagram showing a system for hand hygiene monitoring that includes a remote analysis server in network communication with a plurality of sensors for detecting a hand hygiene action at a hand hygiene device.

One such embodiment of a hand hygiene monitoring system 100 that may monitor hand hygiene compliance, such as may be administered throughout a healthcare facility, is diagrammatically illustrated in FIG. 1. The illustrative hand hygiene monitoring system 100 includes a remote analysis server 102 communicatively coupled via a network 106 to a plurality of sensor equipped devices that will be described in further detail below, which are additionally coupled to equipment located within the facility. For example, an illustrative room 108 (e.g., a hospital room in a healthcare facility) includes a disinfectant hand rub dispenser device 120 located outside the room 108 (i.e., accessible to entrants as they enter the room 108) and another disinfectant hand rub dispenser device 120 located inside the room 108.

The disinfectant hand rub dispenser devices 120 may be embodied as any device or mechanism, manual and/or automatic, configured to dispense disinfectant hand rub (i.e., not a soap and water hand-washing device). It should be appreciated that fewer or additional disinfectant hand rub dispenser devices 120 may be available in alternative embodiments. It should be further appreciated that the disinfectant hand rub dispenser devices 120 may be located in alternative locations relative outside or inside the room 108, in other embodiments. Furthermore, it should be appreciated that a healthcare facility has a multitude of rooms, similar to the illustrative room 108, which may include disinfectant hand rub dispenser devices 120 inside and/or outside some or all of the rooms.

Additionally, the illustrative room 108 includes a soap dispensing device 112 in a bathroom 110 located inside the room 108, as well as another soap dispensing device 112 in another bathroom 136 located external to the room 108. The soap dispensing devices 112 may be embodied as any type of device or mechanism capable of dispensing soap and performing the functions described herein. It should be appreciated that fewer or additional soap dispensing devices 112 may be available in alternative embodiments. It should be further appreciated that the soap dispensing devices 112 may be located in alternative locations than shown in FIG. 1, in other embodiments.

As shown in the illustrative hand hygiene monitoring system 100, a hand hygiene monitoring device 114 is coupled to each of the hand hygiene devices (i.e., the soap dispensing devices 112 and the disinfectant hand rub dispenser devices 120). The hand hygiene monitoring device 114 may be embodied as any combination of software, firmware, and/or hardware circuitry capable of performing the functions described herein, such as monitoring usage of the hand hygiene device to which the hand hygiene monitoring device 114 has been coupled. In use, the hand hygiene monitoring device 114 is configured to detect usage of the hand hygiene device by a staff member 122 (e.g., a caregiver of a healthcare facility) and generate data corresponding to the hand hygiene monitoring device 114 and the staff member 122 for transmission to an external computer (e.g., the remote analysis server 102), which will be described further below. To do so, each of the hand hygiene monitoring devices 114 includes network communication circuitry 116 and reader circuitry 118.

The network communication circuitry 116 may be embodied as any communication circuit, device, or collection thereof, capable of enabling communications over the network 106 to and from the hand hygiene monitoring device 114 (e.g., between the remote analysis server 102 and the hand hygiene monitoring device 114). The network communication circuitry 116 may be configured to use any one or more communication technologies (e.g., wired and/or wireless communication technologies) and associated protocols (e.g., Ethernet, Bluetooth®, Wi-Fi®, WiMAX, etc.) to effect such communication.

The reader circuitry 118 may be embodied as any type of circuit, device, or collection thereof, capable of wirelessly interfacing (i.e., communicating) with a wireless communication component (see, e.g., badge 124 of FIG. 1) that includes compatible communication technology. Information from the badge 124, and from receivers with which the badge 124 communicates, may be used to determine the location of the wearer of the badge 124 (e.g., the staff member 122), as well as interaction with certain devices within the designated facility. For example, the reader circuitry 118 is configured to communicate with the badge 124 to retrieve or receive an identifier unique to the badge 124 (e.g., a nurse call/locating badge) that identifies the staff member 122.

The reader circuitry 118 and the badge 124 may be configured using various short-range wireless communication technologies for automatic identification and data capture (AIDC), such as radio frequency identification (RFID). In one such embodiment, the badge 124 may be embodied as an RFID tag (e.g., passive or active) and the reader circuitry 118 may be embodied as an RFID reader (e.g., passive or active). It should be appreciated that the wireless communication technology used between the badge 124 and the reader circuitry 118 may be employed based on a range capability of the wireless communication technology in use, such that the reader circuitry 118 can only communicate with the badge 124 when the badge 124 is in a proximity dictated by the range capability of the wireless communication technology.

The illustrative room 108 further includes a patient support 126. The patient support 126 may be embodied as any type of support for a patient including, but not limited to, a hospital bed, a chair, a lift, a stretcher, and/or any other type of patient support. The illustrative patient support 126 includes a proximity detection device 128. While the illustrative hand hygiene monitoring system 100 only shows a single proximity detection device 128, any number of proximity detection devices 128 may be employed in alternative embodiments. The proximity detection device 128 may be embodied as any type of circuit, device, or collection thereof, capable of detecting a badge (e.g., the badge 124 of a staff member 122) in proximity of the proximity detection device 128. It should be appreciated that the proximity detection device 128 may be on additional and/or alternative pieces of equipment located throughout the room, in other embodiments.

For example, in the illustrative embodiment, the proximity detection device 128 may be used to determine whether the staff member 122 came in proximate contact with the patient support 126 and/or a patient being assigned to the patient support 126. As such, depending on a condition of the patient, an inference of the staff member's 122 exposure to the patient, and the condition thereof, can be based on the proximity of the staff member 122 to the proximity detection device 128 (i.e., a contamination zone 134 that may compromise hand hygiene of the staff member 122 based on the condition and presence of the patient), as detected by the proximity detection device 128. Similar to the hand hygiene monitoring device 114, the proximity detection device 128 includes network communication circuitry 130 and reader circuitry 132. As such, further descriptions of the like components are not repeated herein for clarity of the description with the understanding that the description of the corresponding components provided above in regard to the hand hygiene monitoring device 114 applies equally to the like components of the proximity detection device 128.

In use, the proximity detection device 128 is configured to detect a presence of a staff member 122 and generate data corresponding to the proximity detection device 128 and the staff member 122 for transmission to an external computer (e.g., the remote analysis server 102), which will be described in further detail below. Accordingly, the proximity detection device 128 may be coupled to any component such that the proximate location of the staff member 122 to the proximity detection device 128 can infer contact and/or usage.

The remote analysis server 102 may be embodied as any type of computation or computer device capable of performing the functions described herein, including, without limitation, a server (e.g., stand-alone, rack-mounted, blade, etc.), a network appliance (e.g., physical or virtual), a web appliance, a distributed computing system, a processor-based system, a multiprocessor system, a smartphone, a mobile computing device, a tablet computer, a laptop computer, a notebook computer, and/or a computer.

Figure 2:
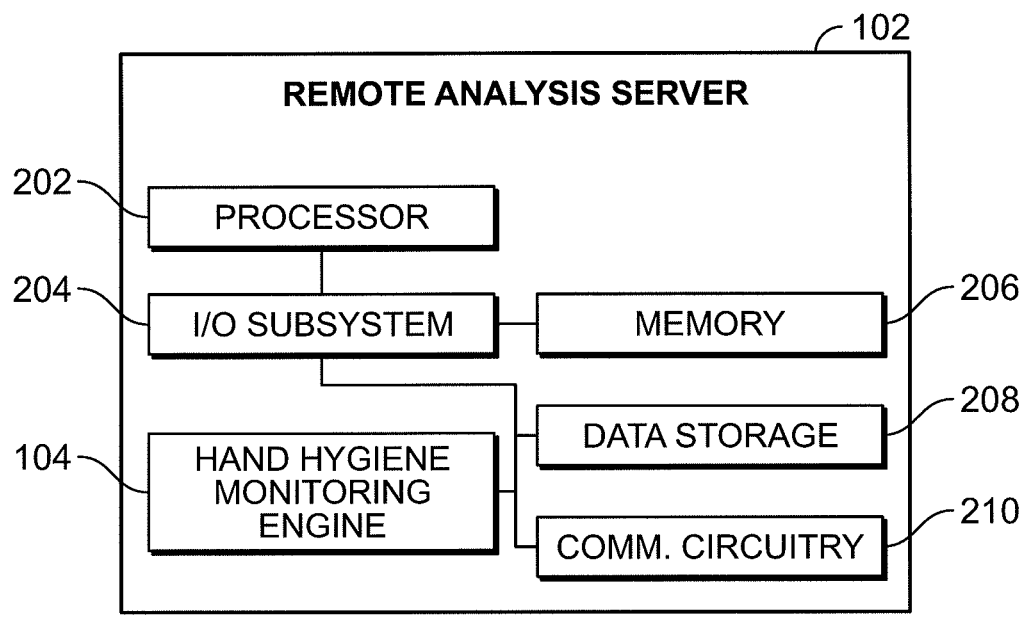
FIG. 2 is a block diagram showing physical components of the remote analysis server of FIG. 1.

As shown in FIG. 2, the illustrative remote analysis server 102 includes a processor 202, an input/output (I/O) subsystem 204, a memory 206, a data storage device 208, and communication circuitry 210, as well as the hand hygiene monitoring engine 104 of FIG. 1. Of course, in other embodiments, the remote analysis server 102 may include other or additional components, such as those commonly found in a computer (e.g., input/output devices, etc.). Additionally, in some embodiments, one or more of the illustrative components may be incorporated in, or otherwise form a portion of, another component. For example, in some embodiments, the memory 206, or portions thereof, may be incorporated in the processor 202.

The processor 202 may be embodied as any type of processor capable of performing the functions described herein. The processor 202 may be embodied as a single or multi-core processor(s), digital signal processor, microcontroller, or other processor or processing/controlling circuit. The I/O subsystem 204 may be embodied as circuitry and/or components to facilitate input/output operations with the processor 202, the memory 206, and other components of the remote analysis server 102. For example, the I/O subsystem 204 may be embodied as, or otherwise include, memory controller hubs, input/output control hubs, integrated sensor hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 204 may form a portion of a system-on-a-chip (SoC) and be incorporated, along with the processor 202, the memory 206, and other components of the remote analysis server 102, on a single integrated circuit chip.

The memory 206 may be embodied as any type of volatile or non-volatile memory or data storage capable of performing the functions described herein. In operation, the memory 206 may store various data and software used during operation of the remote analysis server 102 such as operating systems, applications, programs, libraries, and drivers. The memory 206 is communicatively coupled to the processor 202 via the I/O subsystem 204, which may be embodied as circuitry and/or components to facilitate input/output operations with the processor 202, the memory 206, and other components of the remote analysis server 102. For example, the I/O subsystem 204 may be embodied as, or otherwise include, memory controller hubs, input/output control hubs, integrated sensor hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 204 may form a portion of a system-on-a-chip (SoC) and be incorporated, along with the processors 202, the memory 206, and other components of the remote analysis server 102, on a single integrated circuit chip.

The data storage device 208 may be embodied as any type of device or devices configured for short-term or long-term storage of data such as, for example, memory devices and circuits, memory cards, hard disk drives, solid-state drives, or other data storage devices. The data storage device 208 may include a system partition that stores data and firmware code for the remote analysis server 102. The data storage device 208 may also include an operating system partition that stores data files and executables for an operating system of the remote analysis server 102.

The communication circuitry 210 may be embodied as any communication circuit, device, or collection thereof, capable of enabling communications over the network 106, such as between the remote analysis server 102 and the communication circuitry of the hand hygiene monitoring device 114 and/or the proximity detection device 128. The communication circuitry 210 may be configured to use any one or more communication technologies (e.g., wired and/or wireless communication technologies) and associated protocols (e.g., Ethernet, Bluetooth®, Wi-Fi®, WiMAX, etc.) to effect such communication.

Referring back to FIG. 1, the network 106 may be embodied as any type of wired or wireless communication network, including cellular networks (e.g., Global System for Mobile Communications (GSM), 3G, Long Term Evolution (LTE), Worldwide Interoperability for Microwave Access (WiMAX), etc.), digital subscriber line (DSL) networks, cable networks (e.g., coaxial networks, fiber networks, etc.), telephony networks, local area networks (LANs) or wide area networks (WANs), global networks (e.g., the Internet), or any combination thereof. Additionally, the network 106 may include any number of may include additional computing devices (i.e., networking devices) (not shown), physical and/or virtual, that may be commonly found in networks, such as servers, switches, routers, access points, network controllers, etc.

Figure 3:
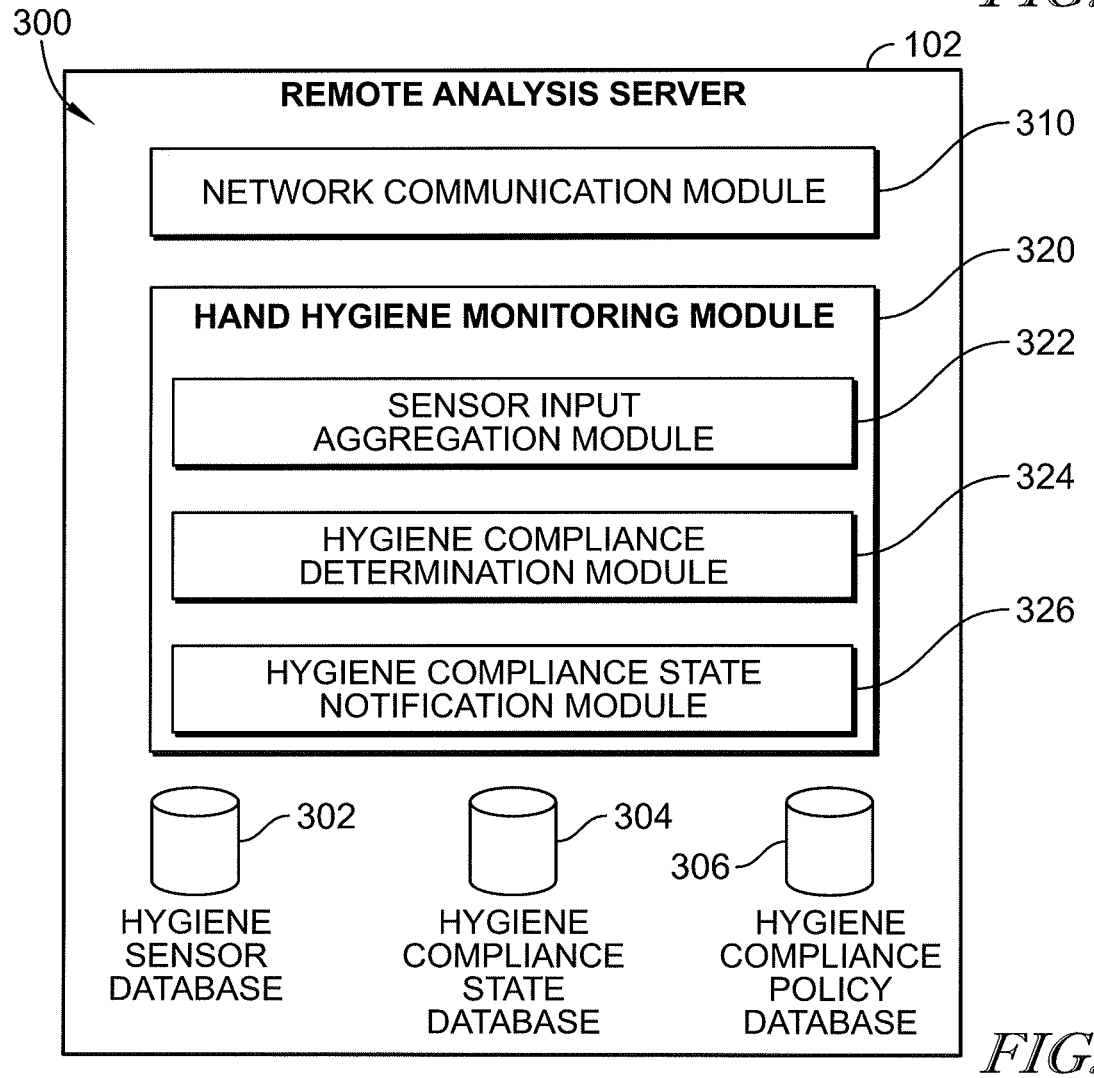
FIG. 3 is a block diagram of an environment that may be established by the remote analysis server of FIGS. 1 and 2.

Referring now to FIG. 3, in an illustrative embodiment, the remote analysis server 102 establishes an environment 300 during operation. The illustrative environment 300 includes a network communication module 310 and a hand hygiene monitoring module 320. Each of the modules, logic, and other components of the environment 300 may be embodied as hardware, software, firmware, or a combination thereof. For example, each of the modules, logic, and other components of the environment 300 may form a portion of, or otherwise be established by, the processor 202 or other hardware components of the remote analysis server 102. As such, in some embodiments, one or more of the modules of the environment 300 may be embodied as a circuit or collection of electrical devices (e.g., network communication circuitry 310, hand hygiene monitoring circuitry 320, etc.).

In the illustrative environment 300, the remote analysis server 102 includes a hygiene sensor database 302, a hygiene compliance state database 304, and a hygiene compliance policy database 306, each of which may be accessed by the various modules and/or sub-modules of the remote analysis server 102. It should be appreciated that the remote analysis server 102 may include other components, sub-components, modules, sub-modules, and/or devices commonly found in a server, which are not illustrated in FIG. 3 for clarity of the description.

The network communication module 310 is configured to facilitate inbound and outbound network communications (e.g., network traffic, network packets, network flows, etc.) to and from the remote analysis server 102. To do so, the network communication module 310 is configured to receive and process network packets from other computers (e.g., the hand hygiene monitoring device 114, the proximity detection device 128, etc.). Additionally, the network communication module 310 is configured to prepare and transmit network packets to other computers (e.g., the hand hygiene monitoring device 114, the proximity detection device 128, etc.). Accordingly, in some embodiments, at least a portion of the functionality of the network communication module 310 may be performed by the communication circuitry 210.

The hand hygiene monitoring module 320 is configured to determine whether a staff member 122 (e.g., a caregiver of a healthcare facility) is in compliance with a hygiene compliance policy assigned to that staff member 122. To do so, the illustrative hand hygiene monitoring module 320 includes a sensor input aggregation module 322, a hygiene compliance determination module 324, and a hygiene compliance state notification module 326. It should be appreciated that at least a portion of the functions performed by the hand hygiene monitoring module 320 as described herein may be executed by the hand hygiene monitoring engine 104.

The sensor input aggregation module 322 is configured to receive and aggregate hygiene sensor data from the various sensors of the hand hygiene monitoring system 100, such as the reader circuitry 118 of the hand hygiene monitoring device 114 and the reader circuitry 132 of the proximity detection device 128. The hygiene sensor data may include any data that is indicative of a detected usage of a hand hygiene device (e.g., the hand hygiene monitoring device 114 or the proximity detection device 128). The hygiene sensor data may include, but is not limited to, a time of the detected usage, an identifier of the staff member 122 that was detected in connection with the usage, an identifier of the hand hygiene device, an identifier of the location (e.g., room and/or identifier associated with the room by the server 102) of the hand hygiene device, and/or a type of the hand hygiene device. In some embodiments, such hygiene sensor data may be stored in the hygiene sensor database 302. As will be described further below, upon receiving the hygiene sensor data, the sensor input aggregation module 322 is further configured to either increment a compliance counter associated with the staff member 122 or reset the compliance counter associated with the staff member 122.

The hygiene compliance determination module 324 is configured to analyze the hygiene sensor data to determine whether the staff member 122 is in compliance with a particular hygiene compliance policy associated with the staff member 122. Accordingly, in some embodiments, the hygiene compliance determination module 324 may be configured to retrieve the hygiene sensor data from the hygiene sensor database 302, retrieve the hygiene compliance policy associated with the staff member 122 from the hygiene compliance policy database 306, and/or make a determination as to whether the staff member 122 is in compliance with the hygiene compliance policy based on the retrieved hygiene sensor data.

Typically, the hygiene compliance policy includes a value that indicates a threshold (e.g., a non-compliance threshold) that may be used to determine whether the staff member 122 is in compliance with the hygiene compliance policy or not. To do so, the hygiene compliance determination module 324 can compare the compliance counter associated with the staff member 122 with the non-compliance threshold to determine whether the staff member 122 is in compliance with the hygiene compliance policy. In some embodiments, the result of the comparison (i.e., a state or present level of compliance of the staff member 122) may be stored in the hygiene compliance state database 304.

The hygiene compliance state notification module 326 is configured to generate a notification indicative of a present state of compliance of the staff member 122 with the hygiene policy. The generated notification may be a signal transmitted to an audible and/or visual indicator that is capable of receiving and interpreting the signal to perform a task associated with the signal (i.e., display a message corresponding to the signal, play an audio clip corresponding to the signal, etc.). For example, the notification may be an alphanumeric message sent to a portable wireless communication device, such as a smartphone, a pager, a PDA, a wireless communication badge (e.g., the badge 124), a wireless phone handset, or any other portable wireless device having message display and/or audio playback capability.

As described further below, there may be various states associated with the compliance of the staff member 122 with regards to the hygiene policy, such as an in-compliance state, a warning of pending non-compliance state, a non-compliance state, etc. In such embodiments, the signal generated by the hygiene compliance state notification module 326 may be transmitted via the network communication module 310 to an external device capable of performing the task associated with the signal. Such external devices may include the hand hygiene monitoring device 114, the caregiver's 122 badge 124, a mobile computing device carried by the staff member 122, and/or any other device capable of providing visual and/or audible notifications.

Figure 4:
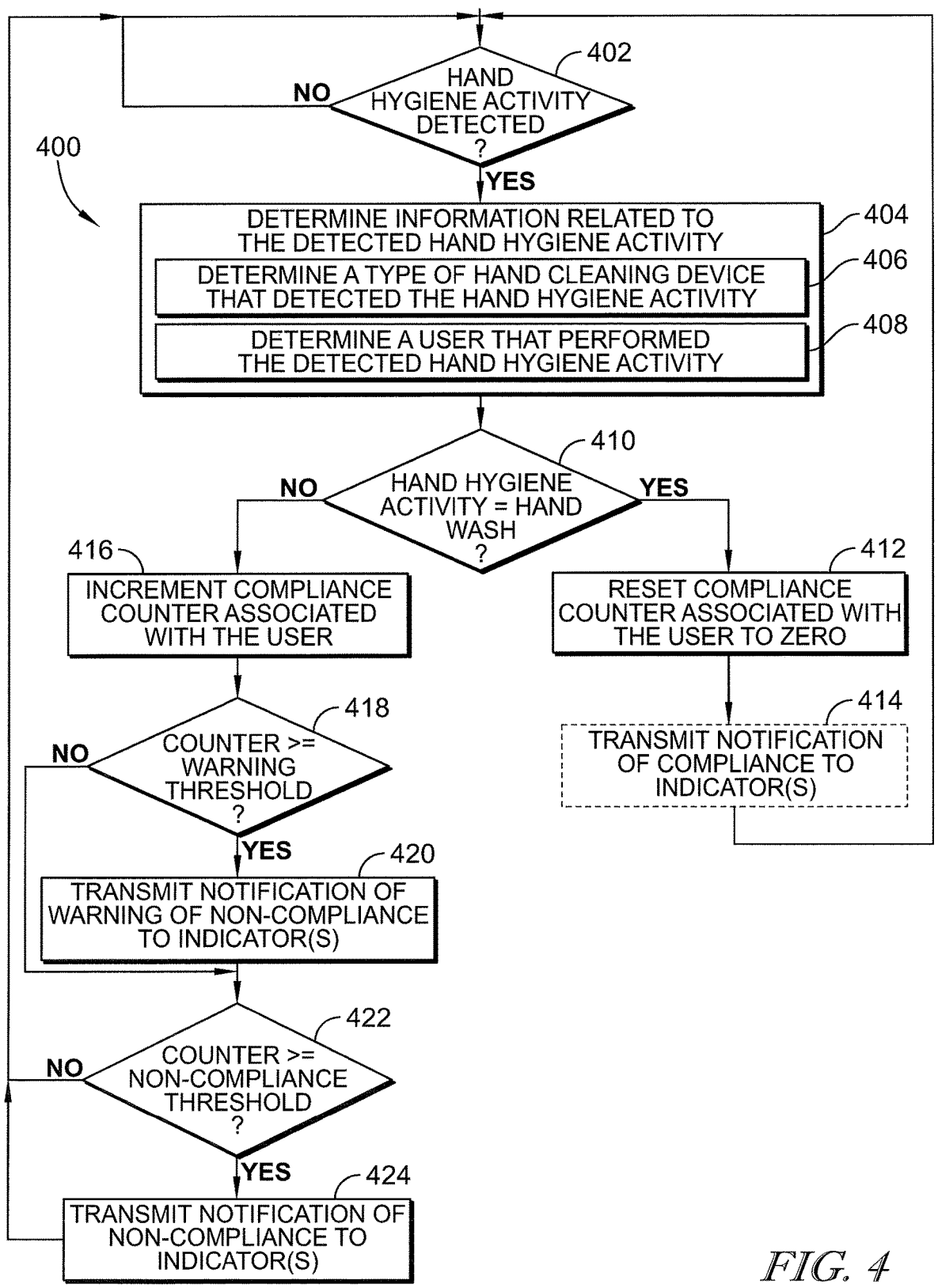
FIG. 4 is a flow diagram of an embodiment of a method for monitoring compliance with a hygiene compliance policy that may be executed by the remote analysis server of FIGS. 1 and 2.

Referring now to FIG. 4, in use, the remote analysis server 102 may execute a method 400 for monitoring compliance of a hygiene compliance policy. It should be appreciated that at least a portion of the method 400 may be executed or otherwise processed by the hand hygiene monitoring engine 104 of the remote analysis server 102. The method 400 begins with step 402, in which the remote analysis server 102 determines whether a hand hygiene activity was detected. In some embodiments, an indication of the hand hygiene activity may be received at the remote analysis server 102 indicating that the hand hygiene activity occurred, such as via a signal transmitted from one of the hand hygiene monitoring devices 114. If the remote analysis server 102 determines the hand hygiene activity was not detected, the method 400 returns to step 402. Otherwise, if the remote analysis server 102 determines the hand hygiene activity was detected, the method 400 advances to step 404.

In step 404, the remote analysis server 102 determines information related to the detected hand hygiene activity. To do so, in step 406, the remote analysis server 102 determines which type of hand cleaning device that notified the remote analysis server 102 of the hand hygiene activity (e.g., a soap dispensing device 112 or a hand hygiene monitoring device 114). In some embodiments, an identifier of the hand cleaning device that detected the hand hygiene activity may be received with the indication to identify the type of hand hygiene activity. Accordingly, the identifier may be indicative of which hand cleaning device notified the remote analysis server 102 of the hand hygiene activity (e.g., a make and/or model of the hand cleaning device, a value designated to a type of the hand cleaning device, etc.). Further, in step 408, the remote analysis server 102 determines a user (e.g., the staff member 122) that performed hand hygiene activity detected in step 402.

From step 408, the method 400 proceeds to step 410, wherein the remote analysis server 102 determines whether the hand hygiene activity can be classified as a hand washing activity. To do so, the remote analysis server 102 determines whether the hand cleaning device that notified the remote analysis server 102 of the hand hygiene activity was a soap dispensing device 112. It should be appreciated that any device associated with the act of a user washing their hands may be used in addition to, or as an alternative to, the soap dispensing device 112.

If the remote analysis server 102 determines the hand cleaning device that notified the remote analysis server 102 of the hand hygiene activity at step 410 was a soap dispensing device 112, the method 400 branches to step 412. In step 412, the remote analysis server 102 resets a compliance counter associated with the user to zero. In some embodiments, in step 414, the remote analysis server 102 may transmit a notification of compliance to one or more visual and/or audio indicators capable of indicating to the user that the user is in compliance with the hand hygiene policy.

If the remote analysis server 102 determines the hand cleaning device that notified the remote analysis server 102 of the hand hygiene activity at step 410 was not a soap dispensing device 112 (e.g., the hand cleaning device is one of the disinfectant hand rub dispenser devices 120 of FIG. 1), the method 400 branches to step 416. In step 416, the remote analysis server 102 increments the compliance counter associated with the user. In step 418, the remote analysis server 102 determines whether the compliance counter is greater than or equal to a warning threshold, which may be established by the hand hygiene policy for which the user is to be in compliance with. If so, the method 400 advances to step 420, wherein the remote analysis server 102 transmits a notification of a warning of pending non-compliance to one or more visual and/or audio indicators capable of indicating to the user that the user is close to not being in compliance with the hand hygiene policy, before advancing to step 422. Otherwise, if the remote analysis server 102 determines that the compliance counter is greater than or equal to the warning threshold, the method 400 proceeds to step 422.

In step 422, the remote analysis server 102 determines whether the compliance counter is greater than or equal to a non-compliance threshold. The non-compliance threshold, similar to the warning threshold, may be established by the hand hygiene policy for which the user is to be in compliance with. Further, the non-compliance threshold is greater than the warning threshold. If the remote analysis server 102 determines the compliance counter is less than the non-compliance threshold, the method returns to step 402. Otherwise, if the remote analysis server 102 determines the compliance counter is greater than or equal to the non-compliance threshold, the method advances to step 424. In step 424, the remote analysis server 102 transmits a notification of non-compliance to one or more visual and/or audio indicators capable of indicating to the user that the user is not in compliance with the hand hygiene policy, before the method 400 returns to step 402.

Figure 5:
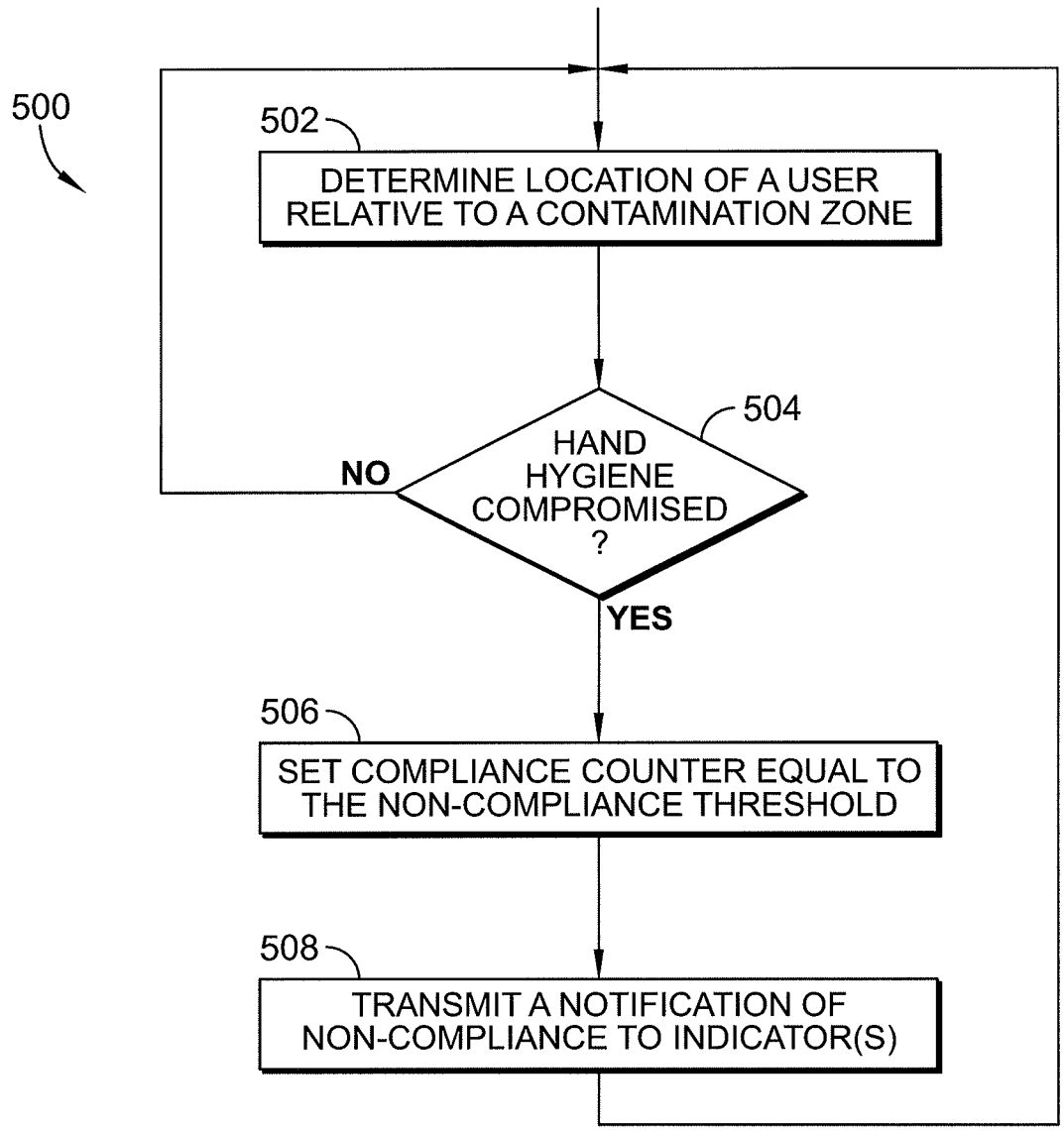
FIG. 5 is a flow diagram of an embodiment of a method for determining whether hand hygiene has been compromised that may be executed by the remote analysis server of FIGS. 1 and 2.

Referring now to FIG. 5, in use, the remote analysis server 102 may execute a method 500 for determining whether hand hygiene has been compromised. It should be appreciated that at least a portion of the method 500 may be executed or otherwise processed by the hand hygiene monitoring engine 104 of the remote analysis server 102. The method 500 begins with step 502, in which the remote analysis server 102 determines a location of a user relative to a contamination zone (e.g., the contamination zone 134 of FIG. 1).

To do so, the remote analysis server 102 may be configured to monitor the proximity detection device 128. In other words, if the user comes within range of the proximity detection device 128, the proximity detection device 128 may provide an indication (e.g., a signal with data) indicative of the user and the location of the proximity detection device 128. Accordingly, in some embodiments, an analysis may be performed using additional information (e.g., a condition of a patient, a presence of the patient in the contamination zone, etc.) provided to the remote analysis server 102 to determine whether such exposure to the user was to an active contamination zone. As such, the remote analysis server 102 can make a determination as to whether hand hygiene of the user has potentially been compromised.

In step 504, the remote analysis server 102 determines whether the hand hygiene was compromised based on the location of the user relative to a contamination zone as determined in step 502. If not, the method 500 returns to step 502. Otherwise, if the remote analysis server 102 determines the hand hygiene was compromised, the method 500 proceeds to step 506. In step 506, the remote analysis server 102 sets the compliance counter equal to the non-compliance threshold, each of which were described in method 400. In step 508, the remote analysis server 102 transmits a notification of non-compliance to one or more visual and/or audio indicators capable of indicating to the user that the user is not in compliance with the hand hygiene policy, before the method 500 returns to step 502.

It should be appreciated that, in some embodiments, the remote analysis server 102 may monitor a positioning coordinate of the user relative to known contamination zones of the room 108, or the facility housing the room 108, for example, based on one or more location determinative sensors of the hand hygiene monitoring system 100. In such embodiments, the location may be determined using a series of proximity sensors spatially located to provide a present position of a user based on their badge, a mobile computing device capable of reporting global positioning system (GPS) coordinates, etc.

Based on the foregoing, it will be appreciated that the system 100 of FIG. 1 is able to distinguish between a soap and water handwashing event and a disinfectant hand rub disinfecting event. For example, a handwashing policy may be established in which a staff member 122 is required to use soap and water for handwashing after the caregiver has used a disinfectant had rub an maximum number of times (e.g., five times). In other words, a staff member 122 will be considered in compliance with the policy as long as they use one of the disinfectant hand rub dispenser devices 120 no more than the maximum number of times and then use one of the soap dispensing devices 112 prior to using one of the disinfectant hand rub dispenser devices 120 again (e.g., a sixth time); otherwise, the staff member 122 will not be considered in compliance with the policy.

Figure 6:
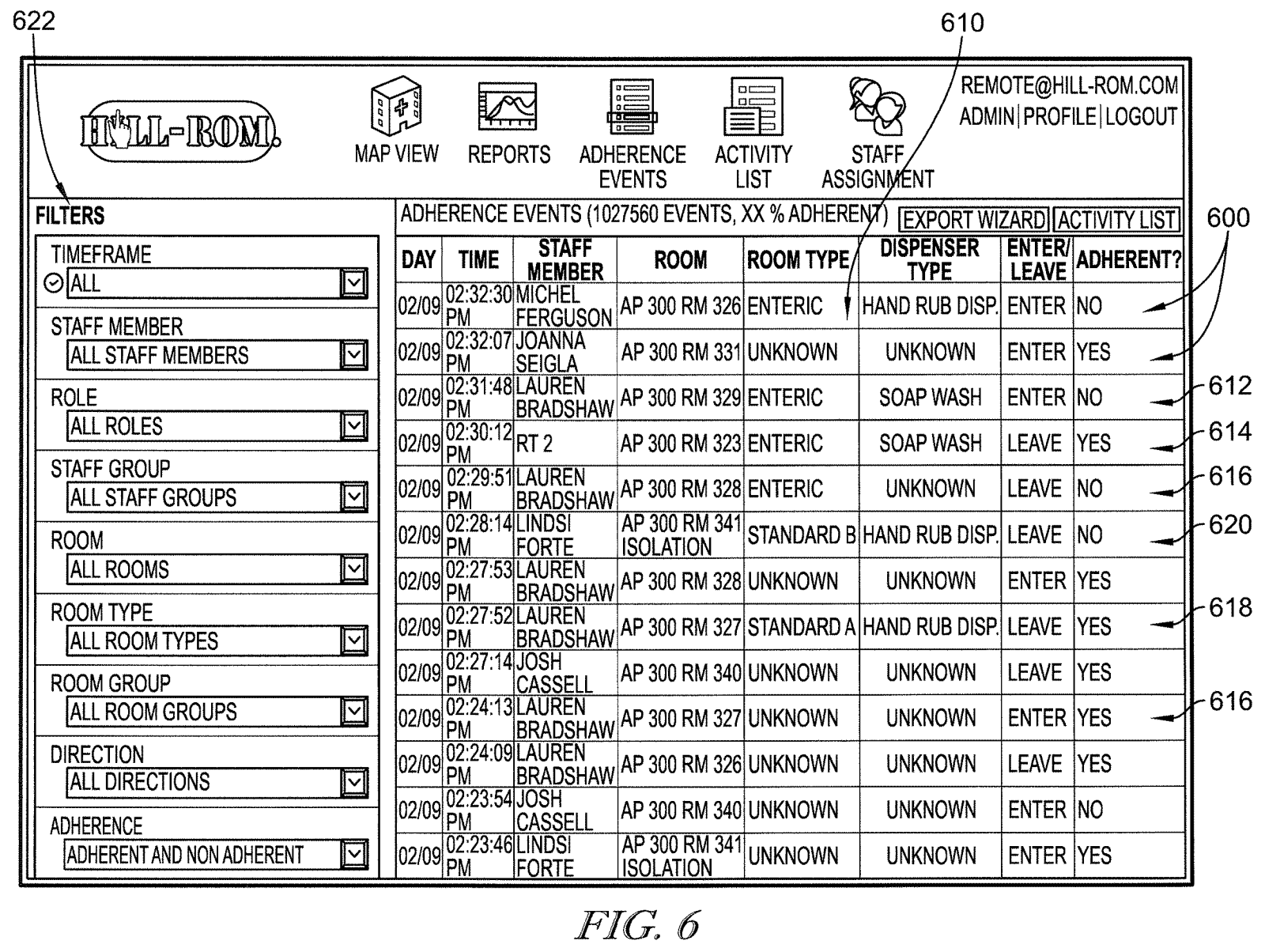

Referring now to FIGS. 6-10, illustrative graphical displays showing information regarding states of compliance ("adherence") to the hygiene compliance policy are shown. As shown in FIG. 6, a graphical display illustratively shows information regarding the hand hygiene monitoring system 100 including adherence events 600 and adherence reports 640, 650, 660, 670 as described herein. In the illustrative embodiment, the graphical displays illustratively depicted in FIGS. 6-10 include displays presented on a caregiver workstation which may be embodied as any one or more of a smartphone, a mobile computing device, a tablet computer, a laptop computer, a notebook computer, and/or a computer. In the illustrative embodiment, the graphical display are illustratively embodied as software and/or hardware wholly maintained and accessed over network 106, but in some embodiments may include software installed on the caregiver workstation.

As illustrated in reference to FIG. 6, the hand hygiene monitoring system 100 is illustratively configurable to apply customizable hygiene protocols in determining compliance. As described above, the hand hygiene monitoring system 100 illustratively determines whether a staff member is in compliance with the hygiene compliance policy based on information received such as hygiene sensor data. The hygiene compliance policy illustratively includes a value that indicates a threshold (i.e., compliance threshold) that can be compared to the hygiene sensor data (illustratively as a compliance counter) to determine hygiene compliance. Allowing customization of thresholds values for compliance under the hand hygiene policy provides the stringency of the protocols to vary according to the associated hygiene risk, for example, requiring handwashing in lieu of hand rub disinfectant. Such customizable hygiene compliance protocols provide a degree of hygiene control over disinfectant resistant hygiene issues, for example, patients with known or suspected *Clostridium difficile* infection ("CDiff patients").

In the illustrative embodiment, the hand hygiene monitoring system 100 determines the value that indicates the threshold for compliance based on a room type designation of the hygiene sensor data as suggested in FIG. 6. As mentioned above, the hygiene sensor data illustratively includes an identifier of the location (e.g., room) of the hand hygiene device. The identifier of the location (e.g., room) of the hand hygiene device illustratively includes an identification of the room type as either "standard" or "enteric." The hand hygiene monitoring system 100 illustratively determines the value indicating the threshold by evaluating a lookup chart or other database maintained and accessible by the remote analysis server 102 based on the room type.

In some embodiments, the hand hygiene monitoring system 100 may determine the value indicating the threshold by execution of an algorithm. In some embodiments, the hand hygiene monitoring system 100 may determine the value indicating the threshold based on any of room type, patient condition, hygiene sensor data, and/or combinations thereof. In some embodiments, room type may be determined directly and/or indirectly based on information stored and retrieved from others systems in communication with the remote analysis server 102 through network 106 (e.g., a medical records repository) and/or based on caregiver inputs to remote analysis server 102 (e.g., direct assignment via a nurse station and/or caregiver interface local or remote to the patient room 108). In some embodiments, the room type designation may be maintained, stored, and/or communicated to the network 106 separately from hygiene sensor data.

In the illustrative embodiment, a room type being designated as "enteric" corresponds to a requirement for caregivers to wash their hands with soap to meet the hand hygiene compliance policy (e.g., disinfectant hand rub is alone insufficient). In the illustrative embodiment, hand hygiene monitoring system 100 receives hygiene sensor data indicating an "enteric" room type designation. The hygiene monitoring system 100 illustratively determines that compliance has been achieved upon a determination that a hand hygiene activity was a hand washing activity (e.g., not alone a disinfectant hand rub activity). In the illustrative embodiment, such compliance includes determining that the type of hand washing device that provided notice of the hand cleaning activity was a soap dispensing device 112. In some embodiments, the hand hygiene policy may include any variation of hygiene requirement, for example, any number of allowable disinfectant hand rub activities permissible before a soap hand washing activity.

As shown in FIG. 6, a graphical display is shown indicating compliance events as hygiene adherence events 600. In the illustrative embodiment, the hygiene adherence events 600 include information indicating the state of compliance according to the hand hygiene activities for a number of rooms 108. As shown in FIG. 6, each adherence event 600 illustratively include the indicated date, time, staff member, room number, room type, dispenser type, proximity event (entrance and exits from proximity sensors), and indication of adherence or not.

In the illustrative embodiment, one adherence event 610 indicates that room number 326 has a room type designated as an "enteric" that illustratively requires handwashing (i.e., disinfectant hand rub is alone insufficient) upon exiting the range of the proximity sensor 128. As shown in FIG. 6, at time 2:32:30 pm the hand hygiene monitoring system 100 determined that a disinfectant hand rub dispenser ("Hand Rub Disp.") was activated. However, disinfectant hand rub did not meet the compliance policy under the associated conditions as illustrated by the adherence column displaying "No."

Another adherence event 612 is shown to indicate that room number 329 is designated as an "enteric" room type. The hand hygiene monitoring system 100 illustratively determined that a soap handwashing event occurred at 2:31:48 pm. In the illustrative embodiment, adherence event 612 is indicated as an "enter" event indicating that the hand hygiene monitoring system 100 did not determine the event was an "exit" Because soap washing is required on "exit" to establish compliance with the policy, "No" in shown in the adherence column.

Another adherence event 614 is shown to indicate that room number 323 is designated as an "enteric" room type and had a successful adherence event at 2:30:12 pm. Because adherence event 614 has an "enteric" room type designation, compliance with the hand hygiene policy was achieved by a soap handwashing event corresponding to an "exit" event.

Several adherence events 616 are shown to include one or more columns indicating an "unknown" entry. In the illustrative embodiment, rooms which have an "enteric" room type designation but include some "unknown" entry are illustratively deemed by the hand hygiene policy as non-compliant as a default. Rooms with "unknown" room type designations are illustratively determined to be compliant based on default conditions as determined by the hand hygiene policy. In some embodiments, the default settings may be adjustable and/or configurable within the hand hygiene policy.

Other adherence events 618, 620 indicate that rooms 327 and 341 have respective room type designations as "Standard A" and "Standard B." In the illustrative embodiment, the standard designation represents less stringent hand hygiene protocols than the "enteric" room type designation. "Standard A" and "Standard B" illustratively include different customizable requirements, but in some embodiments, any number of customized room types may be defined according to the hand hygiene policy. Each of adherence events 618, 620 indicate that a disinfectant hand rub activity occurred in their respective rooms, however, the hand hygiene activity was compliant for the Standard A designation for room 327, but was not compliant for the Standard B designation of room 341. In the illustrative embodiment, the disinfectant hand rub activity of adherence event 620 exceeded the compliance threshold for non-soap handwashing activities, which is illustratively a lower value than that for the Standard A designation.

As shown in FIG. 6, a number of filters 622 permit a user to organize the information displayed according to various selections. Filters 622 illustratively include selectable inputs for timeframe (e.g., range of events dates and times), staff member, roles (e.g., director, nurse tech, radiology, respiratory therapist, RN, surgical services, unit secretary), staff member groups (e.g., staff members having certain common group designations, for example, intensive care), rooms, room types, room groups (e.g., rooms having certain common group designations, for example, cardiac), direction (e.g.), and/or adherence (e.g., indication of compliance). In some embodiments, any number of organizational tools may be included to manage, access, sort, evaluate, apply, communicate, audit and/or investigate information of hand hygiene monitoring system 100.

Figure 7:
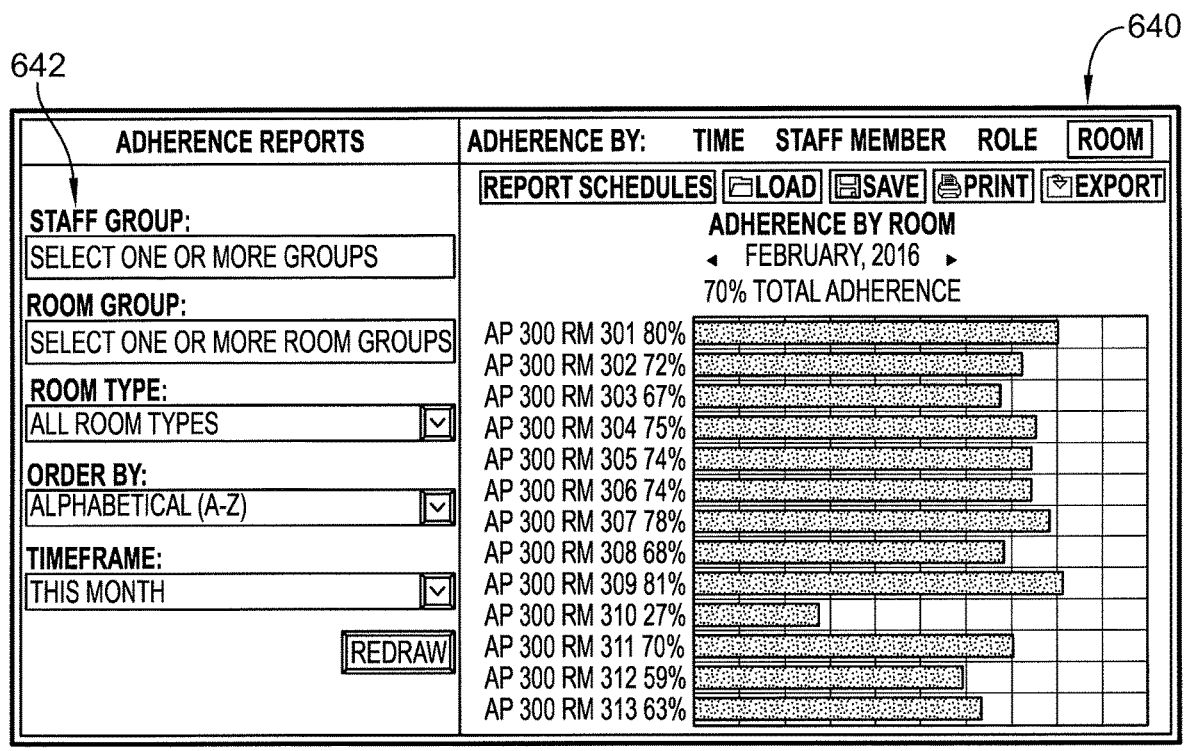
FIG. 7 is a pictorial view of another graphical display of the hand hygiene monitoring system of FIGS. 1 and 2 showing that information regarding hygiene events can be organized for evaluation according to room number.

As shown in FIGS. 7-10, graphical displays show various adherence reports 640, 650, 660, 670. In FIG. 7, an adherence report 640 is illustratively shown as organized according to room number. Filter criteria 642 permits additional organization of adherence report 640 and illustratively includes selectable inputs for room type, order, and timeframe and search text entry fields for staff group and room group. The adherence report 640 is illustratively shown as filtered according to a timeframe of the current month ("this month"). In the illustrative embodiment, the percentage of adherence for each room is indicated as a bar graph comprising values determined according to the room type designation such that rooms which are designated as "enteric" or "standard" room types are evaluated against their respective thresholds according to the hand hygiene policy.

Figure 8:
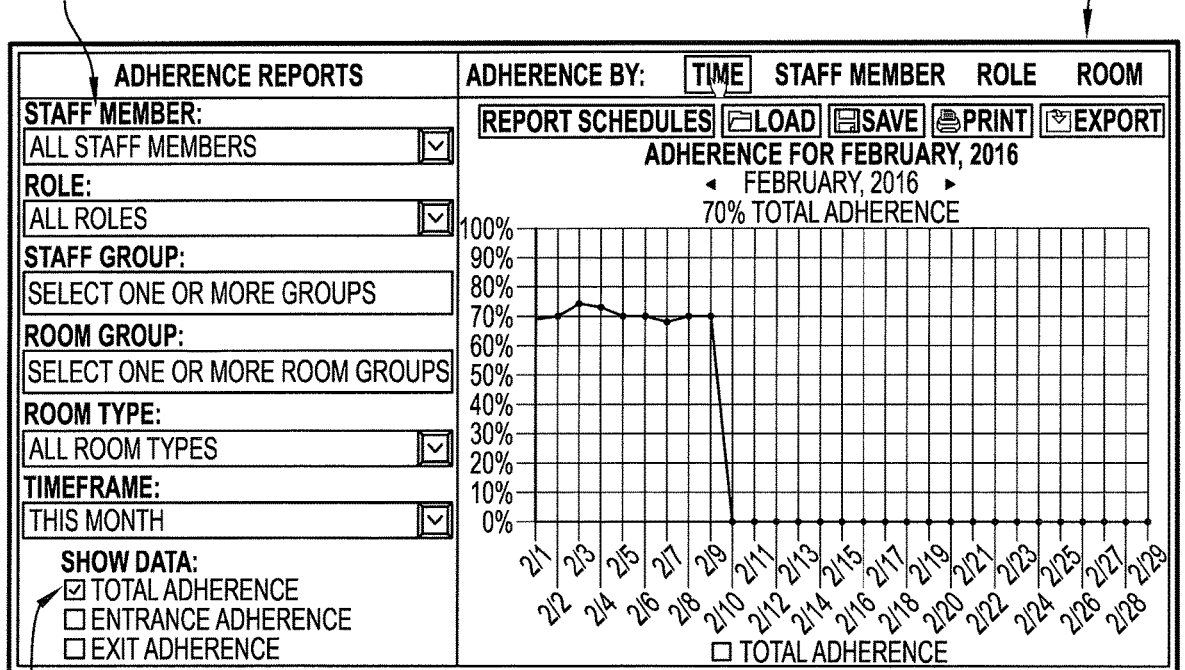
FIG. 8 is a pictorial view of another graphical display of the hand hygiene monitoring system of FIGS. 1 and 2 showing that information regarding hygiene events can be organized for evaluation according to time.

In FIG. 8, an adherence report 650 is illustratively shown as organized according to time, specifically by days. Filter criteria 652 permits additional organization of adherence report 650 and illustratively includes selectable inputs for room type, staff member, and timeframe and search text entry fields for staff group and room group. Filter criteria 652 illustratively includes selectable boxes 654 which illustratively include options for delimiting the information to any one or more of total adherence, exit adherence events, and entrance adherence events. The adherence report 650 is illustratively shown as filtered according to a timeframe of the current month ("this month"). In the illustrative embodiment, the percentage of adherence for each day is indicated as a line graph comprising values determined according to the room type designation such that rooms which are designated as "enteric" or "standard" room types are evaluated against their respective thresholds according to the hand hygiene policy.

Figure 9:
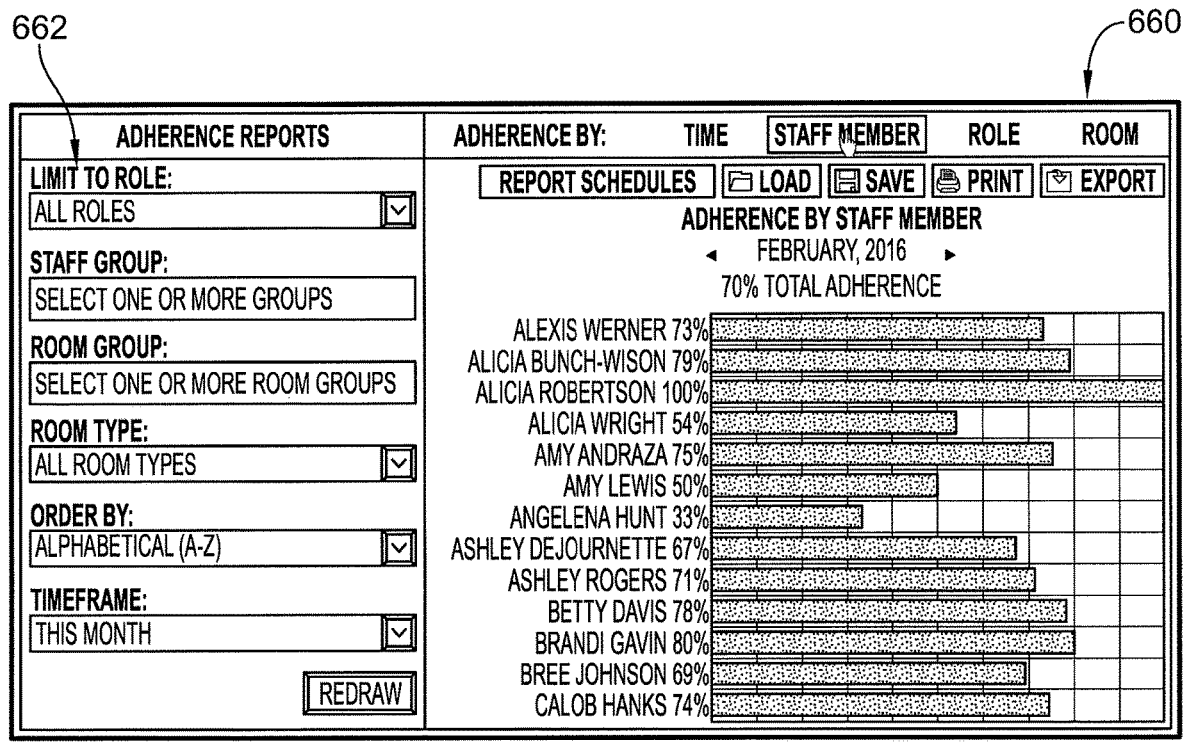
FIG. 9 is a pictorial view of another graphical display of the hand hygiene monitoring system of FIGS. 1 and 2 showing that information regarding hygiene events can be organized for evaluation according to staff member.

In FIG. 9, an adherence report 660 is illustratively shown as organized according to staff member. Filter criteria 662 permits additional organization of adherence report 660 and illustratively includes selectable inputs for roles, room type, order, and timeframe and search text entry fields for staff group and room group. The adherence report 660 is illustratively shown as filtered according to a timeframe of the current month ("this month"). In the illustrative embodiment, the percentage of adherence for each staff member is indicated as a bar graph comprising values determined according to the room type designation such that rooms which are designated as "enteric" or "standard" room types are evaluated against their respective thresholds according to the hand hygiene policy.

Figure 10:
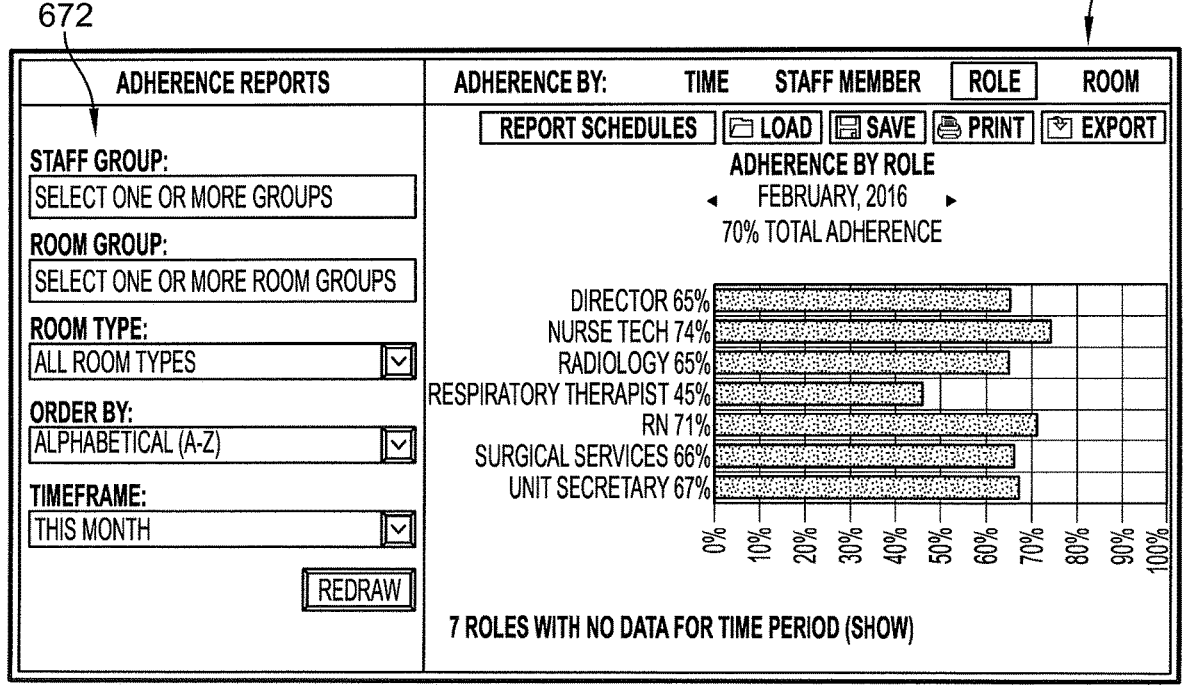
FIG. 10 is a pictorial view of another graphical display of the hand hygiene monitoring system of FIGS. 1 and 2 showing that information regarding hygiene events can be organized for evaluation according to roles.

In FIG. 10, an adherence report 670 is illustratively shown as organized according to role. Filter criteria 672 permits additional organization of adherence report 670 and illustratively includes selectable inputs for room type, order, and timeframe and search text entry fields for staff group and room group. The adherence report 670 is illustratively shown as filtered according to a timeframe of the current month ("this month"). In the illustrative embodiment, the percentage of adherence for each role is indicated as a bar graph comprising values determined according to the room type designation such that rooms which are designated as "enteric" or "standard" room types are evaluated against their respective thresholds according to the hand hygiene policy.

The present disclosure includes devices, systems, and methods of customizing hygiene compliance thresholds and managing, accessing, sorting, evaluating, applying, communicating, auditing and/or investigating information related to hygiene compliance. The present disclosure includes devices, systems, and methods for reducing healthcare associated infections (HAI) by providing audit trails and/or reports to track appropriate hand hygiene relative to isolation-related precautions. Such tracking and auditing permits demonstration of accurate documentation of appropriate hand hygiene procedures by showing correspondence in information such as room type designation. The present disclosure includes description of communicating the hand wash device type as either of soap or disinfectant rub, but in some embodiments may include any number of alternative hand hygiene substances and/or methods.

Although certain illustrative embodiments have been described in detail above, variations and modifications exist within the scope and spirit of this disclosure as described and as defined in the following claims. The drawings are provided to facilitate understanding of the disclosure, and may depict a limited number of elements for ease of explanation. Except as may be otherwise noted in this disclosure, no limits on the scope of patentable subject matter are intended to be implied by the drawings.

The invention claimed is:

1. A method for monitoring hand hygiene compliance with hand hygiene policy, the method comprising:
  receiving, at a remote analysis server, an indication from a first hand hygiene device that a hand hygiene activity was performed by a user of the first hand hygiene device, wherein the indication includes an identifier of the first hand hygiene device and an identifier of the user;
  determining, by a hand hygiene monitoring engine of the remote analysis server, whether the identifier of the first hand hygiene device corresponds to at least one disinfectant hand rub dispensing device and not to one or more soap dispensing devices, and in response to determination that the identifier of the first hand hygiene device corresponds to the at least one disinfectant hand rub dispensing device and not to one or more soap dispensing devices, incrementing, by the hand hygiene monitoring engine, a compliance counter based on the identifier of the user, and in response to determination that the identifier of the first hand hygiene device does not correspond to at least one disinfectant hand rub dispensing device and instead to one or more soap dispensing devices, abstaining from incrementing the compliance counter, comparing, by the hand hygiene monitoring engine, the compliance counter to a non-compliance threshold of the hand hygiene policy to determine whether the non-compliance threshold has been exceeded; and transmitting, by the hand hygiene monitoring engine, a notification of non-compliance in response to a determination that the compliance counter is greater than or equal to the non-compliance threshold.

2. The method of claim 1, further comprising resetting, by the hand hygiene monitoring engine, the compliance counter associated with the user in response to a determination that the identifier of the first hand hygiene device corresponds to one or more soap dispensing devices.

3. The method of claim 2, further comprising transmitting, by the hand hygiene monitoring engine and in response to the compliance counter being reset, a notification of compliance to one or more visual indicators proximate to the user.

4. The method of claim 3, wherein transmitting the notification of non-compliance comprises transmitting the notification of non-compliance to one or more visual indicators proximate to the user.

5. The method of claim 4, wherein the one or more visual indicators includes a visual indicator of at least one of a badge worn by the user, a wrist-worn device worn by the user, a mobile computing device carried by the user, the first hand hygiene device, another first hand hygiene device, and equipment in viewing proximity of the user.

6. The method of claim 1, wherein transmitting the notification of non-compliance comprises transmitting the notification of non-compliance to one or more audible indicators proximately located near the user.

7. The method of claim 6, wherein the one or more audible indicators includes an audible indicator of at least one of a badge worn by the user, a wrist-worn device worn by the user, a mobile computing device carried by the user, the first hand hygiene device, another first hand hygiene device, and equipment in hearing proximity of the user.

8. The method of claim 1, further comprising comparing, by the hand hygiene monitoring engine, the compliance counter to a warning threshold of the hand hygiene policy, wherein the warning threshold is less than the non-compliance threshold; and transmitting, by the hand hygiene monitoring engine, a warning notification of non-compliance in response to a determination that the compliance counter is greater than or equal to the warning threshold.

9. The method of claim 8, wherein transmitting the warning notification of non-compliance comprises transmitting the warning notification of non-compliance to one or more visual indicators proximate to the user.

10. A system for monitoring compliance with hygiene compliance policy, the system comprising:

a plurality of hand hygiene devices, wherein each of the plurality of hand hygiene devices includes a sensor capable of detecting a user at one of the plurality of hand hygiene devices during a usage of the one of the plurality of hand hygiene devices; and a remote analysis server communicatively coupled to each of the plurality of hand hygiene devices, wherein the remote analysis server includes a hand hygiene monitoring engine that is configured to monitor hand hygiene compliance of each user based on the hygiene compliance policy and a compliance counter associated with each user, wherein each of the plurality of hand hygiene devices is further configured to transmit to the remote analysis server an indication that a hand hygiene activity was performed by a user, wherein the indication includes an identifier of the hand hygiene device and an identifier of the user, wherein the hand hygiene monitoring engine, in response to having received the indication, is further configured (i) to determine whether the identifier of the hand hygiene device corresponds to at least one disinfectant hand rub dispensing device and not to one or more soap dispensing devices, and (ii) in response to determination that the identifier of the hand hygiene device corresponds to at least one disinfectant hand rub dispensing device and not to one or more soap dispensing devices to increment a compliance counter based on the identifier of the user in response to determination that the hand hygiene device corresponds to the at least one disinfectant hand rub dispensing device and not to one or more soap dispensing devices, and in response to determination that the identifier of the hand hygiene device does not correspond to at least one disinfectant hand rub dispensing device and instead to one or more soap dispensing devices to abstain from incrementing the compliance counter, and (iii) to compare a value of the compliance counter to a non-compliance threshold to determine whether the user is in compliance with the hygiene compliance policy, and (iv) transmit a notification of non-compliance in response to a determination that the value of the compliance counter is greater than or equal to the non-compliance threshold, and wherein the notification is usable by a receiving device to provide an indication to the user that the user is not in compliance with the hygiene compliance policy.

11. The system of claim 10, wherein the hand hygiene monitoring engine is further configured to reset the compliance counter associated with the user in response to a determination that the identifier of the first hand hygiene device corresponds to one or more soap dispensing devices.

12. The system of claim 11, wherein the hand hygiene monitoring engine is further configured to transmit, in response to the compliance counter being reset, a notification of compliance to one or more visual indicators proximate to the user.

13. The system of claim 12, wherein to transmit the notification of non-compliance comprises transmitting the notification of non-compliance to one or more visual indicators proximate to the user.

14. The system of claim 13, wherein the one or more visual indicators includes a visual indicator of at least one of a badge worn by the user, a wrist-worn device worn by the user, a mobile computing device carried by the user, the first hand hygiene device, another first hand hygiene device, and equipment in viewing proximity of the user.

15. The system of claim 10, wherein to transmit the notification of non-compliance comprises to transmit the notification of non-compliance to one or more audible indicators proximate to the user.

16. The system of claim 15, wherein the one or more audible indicators includes an audible indicator of at least one of a badge worn by the user, a wrist-worn device worn by the user, a mobile computing device carried by the user, the first hand hygiene device, another first hand hygiene device, and equipment in hearing proximity of the user.

17. The system of claim 10, wherein the hand hygiene monitoring engine is further to compare the compliance counter to a warning threshold of the hand hygiene policy, wherein the warning threshold is less than the non-compliance threshold and transmit a warning notification of non-compliance in response to a determination that the compliance counter is greater than or equal to the warning threshold.

18. The system of claim 17, wherein to transmit the warning notification of non-compliance comprises to transmit the warning notification of non-compliance to one or more visual indicators proximate to the user.

19. The system of claim 10, wherein the non-compliance threshold is determined based on a room type designation corresponding to the identifier of the hand hygiene device.

20. The system of claim 19, wherein the room type designation is one of enteric and standard.

21. The system of claim 20, wherein the room type designation is enteric and the non-compliance threshold is one.

22. A system for monitoring compliance with hygiene compliance policy, the system comprising:
a number of hand hygiene devices, each of the hand hygiene devices including a sensor capable of detecting a user at one of the hand hygiene devices during a usage of the hand hygiene device; and
a remote analysis server communicatively coupled to the hand hygiene devices, the remote analysis server including a hand hygiene monitoring engine that is configured to monitor hand hygiene compliance of each user based on the hygiene compliance policy and a compliance counter associated with each user,
wherein each of the plurality of hand hygiene devices is further configured to transmit to the remote analysis server an indication that a hand hygiene activity was performed by a user, the indication including an identifier of the type of hand hygiene device and an identifier of the user,
wherein the hand hygiene monitoring engine is further configured, in response to having received the indication, (i) to determine whether the transmitted identifier from the hand hygiene device corresponds to at least one disinfectant hand rub dispensing device, (ii) in response to determination that the transmitted identifier of the hand hygiene device corresponds to at least one disinfectant hand rub dispensing device, to increment a compliance counter based on the identifier of the user, and in response to determination that the transmitted identifier of the hand hygiene device does not correspond to at least one disinfectant hand rub dispensing device to abstain from incrementing the compliance counter, and (iii) to compare a value of the compliance counter to a non-compliance threshold to determine whether the user is in compliance with the hygiene compliance policy, and (iv) to transmit a notification of non-compliance in response to a determination that the value of the compliance counter is greater than or equal to the non-compliance threshold, wherein the notification is usable by a receiving device to provide an indication to the user that the user is not in compliance with the hygiene compliance policy.

* * * * *